United States Patent [19]

Ross et al.

[11] Patent Number: 5,584,811
[45] Date of Patent: *Dec. 17, 1996

[54] INFUSION PUMP, TREATMENT FLUID BAG THEREFOR, AND METHOD FOR THE USE THEREOF

[75] Inventors: Stephen O. Ross, Vista; Mark D. McWilliams, San Diego, both of Calif.

[73] Assignee: Medication Delivery Devices, Inc., San Diego, Calif.

[*] Notice: The term of this patent shall not extend beyond the expiration date of Pat. No. 5,207,645.

[21] Appl. No.: 503,524

[22] Filed: Jul. 18, 1995

Related U.S. Application Data

[60] Continuation of Ser. No. 238,265, May 3, 1994, Pat. No. 5,433,704, which is a division of Ser. No. 970,299, Nov. 2, 1992, Pat. No. 5,308,335, which is a continuation of Ser. No. 720,658, Jun. 25, 1991, Pat. No. 5,207,645.

[51] Int. Cl.$^6$ .................................................. A61M 5/142
[52] U.S. Cl. ............................................ 604/141; 604/67
[58] Field of Search ................................... 604/140, 141, 604/65, 67

[56] References Cited

U.S. PATENT DOCUMENTS

| | | |
|---|---|---|
| 3,153,414 | 10/1964 | Beal et al. . |
| 3,468,308 | 9/1969 | Bierman et al. . |
| 3,543,753 | 12/1970 | Weinstein . |
| 3,640,276 | 2/1972 | Dancy, Jr. . |
| 3,640,277 | 2/1972 | Adelberg .......................... 128/DIG. 12 |
| 3,884,228 | 5/1975 | Hahn . |
| 3,895,741 | 7/1975 | Nugent .......................... 128/DIG. 12 |
| 3,966,358 | 6/1976 | Heimes et al. . |
| 4,048,994 | 9/1977 | Lo . |
| 4,090,514 | 5/1978 | Hinck et al. . |
| 4,205,676 | 6/1980 | Humphrey et al. . |
| 4,332,246 | 6/1982 | Thompson . |
| 4,337,769 | 7/1982 | Olson . |
| 4,416,595 | 11/1983 | Cromie . |
| 4,430,078 | 2/1984 | Sprague .......................... 128/DIG. 12 |
| 4,507,116 | 3/1985 | Leibinsohn . |
| 4,539,005 | 9/1985 | Greenblatt . |
| 4,613,327 | 9/1986 | Tegrarian et al. ................ 128/DIG. 12 |
| 4,626,243 | 12/1986 | Singh et al. . |
| 4,657,160 | 4/1987 | Woods et al. ............................ 604/141 |
| 4,666,430 | 5/1987 | Brown et al. . |
| 4,673,392 | 6/1987 | Keime . |
| 4,714,462 | 12/1987 | DiDomenico ............................ 604/67 |
| 4,718,893 | 1/1988 | Dorman et al. . |
| 4,734,092 | 3/1988 | Millerd . |
| 4,735,613 | 4/1988 | Bellin et al. . |
| 4,778,451 | 10/1988 | Kamen . |
| 4,781,687 | 11/1988 | Wall . |
| 4,857,055 | 8/1989 | Wang . |
| 4,913,703 | 4/1990 | Pasqualucci et al. . |
| 4,950,245 | 8/1990 | Brown et al. . |
| 4,955,860 | 9/1990 | Ruano . |
| 5,013,303 | 5/1991 | Tamari et al. . |
| 5,053,011 | 10/1991 | Strobel et al. . |
| 5,053,012 | 10/1991 | Edwards et al. . |
| 5,201,711 | 4/1993 | Pasqualucci et al. . |
| 5,246,347 | 9/1993 | Davis . |
| 5,276,610 | 1/1994 | Maeda et al. . |
| 5,318,540 | 6/1994 | Athayde et al. . |
| 5,330,431 | 7/1994 | Herskowitz . |

*Primary Examiner*—Paul J. Hirsch
*Attorney, Agent, or Firm*—Fish & Richardson, P.C.

[57] ABSTRACT

An infusion pump for infusing a medical treatment fluid intravenously to a patient includes a collapsible treatment fluid bag juxtaposed with an inflatable drive fluid bladder confined between a pair of opposing containment members which cause the bladder to impinge against the bag as the bladder is inflated. A drive fluid pump controllably inflates the bladder, thereby displacing treatment fluid from the bag into an outlet tube affixed thereto which conveys the treatment fluid to the patient where it is received intravenously. The treatment fluid flow rate through the tube is controlled by increasing or decreasing the drive fluid pump output and consequently the pressure in the bladder in response to a pressure sensor in fluid communication with the bladder. Alternatively, the treatment fluid flow rate is adjusted by opening or closing the outlet tube by means of an occluder or restrictor positioned along the tube.

29 Claims, 4 Drawing Sheets

INFUSION PUMP, TREATMENT FLUID BAG THEREFOR, AND METHOD FOR THE USE THEREOF

This is a continuation of application Ser. No. 08/238,265, which was filed May 3, 1994, and issued as U.S. Pat. No. 5,433,704 on Jul. 18, 1995, which is a divisional of Ser. No. 07/970,299, filed Nov. 2, 1992, now U.S. Pat. No. 5,308,335 issued on May 3, 1994, which is a continuation of Ser. No. 07/720,658, filed Jun. 25, 1991, now U.S. Pat. No. 5,207,645 issued on May 4, 1993.

FIELD OF THE INVENTION

The present invention relates generally to apparatus and methods for the intravenous infusion of medical treatment fluid to a patient. More particularly, the present invention pertains to a pump for the intravenous infusion of medical treatment fluid to a patient, and methods for the use of such pump. In a particular aspect, the present invention relates to an intravenous infusion pump operated by inflation of a bladder which impinges against a flexible treatment fluid reservoir.

BACKGROUND OF THE INVENTION

Intravenous administration sets which are useful for infusing medical treatment fluids to a patient are well known and widely used. In the most simple configuration, the intravenous fluid administration set includes a fluid source, an intravenous line connecting the fluid source to the patient, and a device operatively associated with the intravenous line to influence the rate of fluid flow to the patient. Flow rate control devices are characterized as either pumps or controllers. Controllers rely on gravity for the flow of treatment fluid through the system, while pumps exert an electro-mechanical force on the fluid to establish a fluid flow.

Pumps are often preferred because they can deliver higher pressures and can accurately deliver a wide range of flow rates. However, pumps have some inherent disadvantages which render them less than ideal, e.g., cost, complexity, size, and (lack of) mobility. There is, therefore, a need for pumps which are relatively small and simple to operate, yet which are relatively accurate and reliable (and which preferably utilize a minimum number of components in the fluid containment and delivery set thereof). The ability to produce such a pump which is portable and which is relatively inexpensive to manufacture would be beneficial in the field of medical treatment fluid delivery, especially in the home care setting.

SUMMARY OF THE INVENTION

In one aspect, the present invention comprises an infusion pump for infusing a medical treatment fluid intravenously to a patient. In another aspect, the present invention comprises a method for infusing intravenous fluid to a patient. In yet another aspect, the present invention comprises novel treatment fluid bags useful with the invention pump.

The invention infusion pump comprises a collapsible treatment fluid bag and an inflatable drive fluid bladder juxtaposed therewith. The invention infusion pump further comprises a control assembly to controllably inflate the bladder, so as to establish (and maintain) a desired pressure in the treatment fluid bag. The treatment fluid bag and bladder are positioned between opposing containment members which cause the bladder to impinge against the bag as the bladder is inflated.

The treatment fluid bag has an outlet tube affixed thereto which enables treatment fluid to exit the bag as it is being collapsibly compressed by impingement of the bladder thereagainst. The outlet tube is in fluid communication with the patient to convey the treatment fluid to the patient where it is received intravenously. The effluent flow rate through said outlet tube can readily be determined once a set pressure is established in the fluid treatment bag, e.g., by using an outlet tube having a predetermined fixed cross-sectional area which is defined by the inside diameter of the tube, or alternatively by a fixed flow restriction positioned along the length of tubing.

The infusion pump of the present invention has numerous advantages over prior art pumps, combining many desirable features such as accuracy, low cost, low power requirements, ease of operation, and the like, into a light-weight, self-contained, relatively small unit. The invention unit can be readily reconfigured in a variety of ways to adapt to the requirements of different therapies. For example, a wide range of flow profiles, rates of fluid delivery, volumes of fluid delivered, and the like, can be accomodated by the invention infusion pump. The invention unit employs a treatment fluid bag which can be readily filled, with treatment fluid administered to the patient by way of a simple, reliable delivery system.

The invention pump and delivery system employing same have certain inherent safety features. For example, the pressure under which the treatment fluid is delivered to the patient is limited by the design of the pump, in contrast to prior art pumps which may expose the patient to the possibility of pressures as high as 35 psi (or higher) in the event of malfunction. In addition, the possibility of free flow of treatment fluid from the treatment fluid bag is substantially eliminated with the invention pump, whereas prior art pumps may subject the patient to the possibility of exposure to a free flow of treatment fluid in the event of malfunction.

The novel features of this invention, as well as the invention itself, both as to its structure and its operation, will be further understood from the accompanying drawings, taken in conjunction with the accompanying description.

BRIEF DESCRIPTION OF THE DRAWINGS

FIG. 9 illustrates two embodiments of multichambered fluid treatment bags contemplated by the present invention.

FIG. 10 illustrates two embodiments of the activator means employed in conjunction with the fluid treatment bag of the present invention.

DETAILED DESCRIPTION OF THE INVENTION

In accordance with the present invention, there is provided a pump for infusing intravenous treatment fluid to a patient. The invention infusion pump comprises:

a collapsible treatment fluid bag;

an inflatable bladder juxtaposed with said treatment fluid bag;

means to vent said bladder;

means for impinging said bladder against said treatment fluid bag as said bladder is inflated;

means for electronically controlling the pressure of said bladder so as to collapse said treatment fluid bag and controllably expel treatment fluid therefrom; and an outlet tube in fluid communication with said treatment fluid bag and said patient.

In accordance with another embodiment of the present invention, there is provided a collapsible fluid treatment bag comprising:

an attached extension set;

activator means capable of interacting with the means for electronically controlling the pressure of said bladder so as to enable the means for electronically controlling the pressure of said bladder to operate; wherein said means for electronically controlling the pressure of said bladder is disabled in the absence of said activator means; and a port for introducing fluid into said treatment bag.

In accordance with yet another embodiment of the present invention, there is provided a method for infusing intravenous treatment fluid to a patient comprising:

positioning an inflatable bladder in juxtaposition with a fluid-containing collapsible treatment fluid bag within a confined containment volume formed by first and second opposing containment members;

controllably inflating said bladder, thereby impinging said bladder against said treatment fluid bag;

collapsing said treatment fluid bag to expel treatment fluid therefrom into an outlet tube in fluid communication with said treatment fluid bag, wherein treatment fluid is controllably expelled from said treatment fluid bag at a predetermined rate; and displacing said treatment fluid through said outlet tube to the patient.

The collapsible treatment fluid bag contemplated for use in the practice of the present invention can be made of materials commonly employed to produce flexible bags of the type conventionally used to retain medical treatment fluids for intravenous infusion. Examples of such materials include polyvinyl chloride (PVC), polyolefins (e.g., polypropylene), polyurethanes, and the like. The treatment fluid bag is preferably filled before placement in the containment means which enables the inflated bladder to impinge the treatment fluid bag. Alternatively, treatment fluid bag can be placed in the containment means, then filled with treatment fluid. The treatment fluid bag can be filled to any suitable volumetric capacity; typically between about 100 ml and 5000 ml.

A variety of shapes are acceptable for the invention fluid treatment bag. Preferably, the bag will have a shape that facilitates the expulsion of air therefrom via the inlet or outlet tube. Shapes which serve this purpose are shapes which provide the bag with a smooth surface wherein substantially no pockets exist that would allow air to become trapped in the bag. Thus, fluid treatment bags having a tapered top surface, a domed top surface, a convex top surface, and the like, are contemplated.

Treatment fluid bags contemplated for use in the practice of the present invention can be viewed as modified versions of conventionally available treatment fluid bags. One such modification is the presence (on invention treatment fluid bags) of activator means capable of interacting with coordinating activator means, optionally included in the control assembly of the above-described infusion pump, so as to enable the control assembly of said pump to operate; wherein the control assembly (in this embodiment of the invention) is disabled in the absence of the activator means, i.e., the activator means is capable of serving as a "safety interlock", thereby preventing the inadvertent use of fluid containers not specifically designed to be used in conjunction with the invention pump. Such inadvertent use is undesirable as it could lead to excessively high flow rates for delivery of treatment fluid to the patient. Thus, the presence of the activator means ensures that the invention pump is operable for the delivery of treatment fluid to the patient only when a treatment fluid bag containing the desired treatment fluid is inserted into the containment means of the pump. Thus, only the desired treatment fluid is delivered to the patient, and such treatment fluid is provided at an appropriate target flow rate. At the same time, delivery of treatment fluids not contemplated for use with the particular configuration (i.e., flow rate, quantity of treatment fluid, etc) of the invention pump is prevented.

Figure 9A:
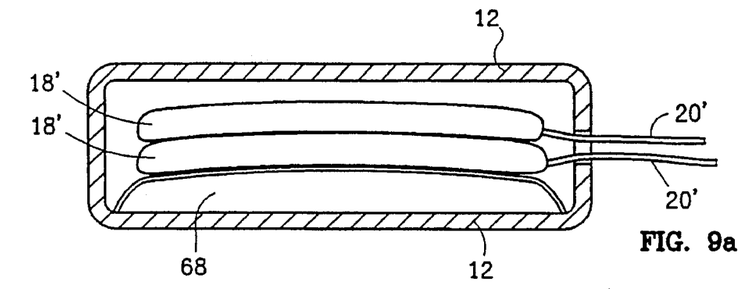
FIG. 9A is a sectional view illustrative of a stacked fluid container arrangement. Specifically shown are two independent fluid chambers positioned between the drive fluid bladder and the containment means.
Figure 9B:
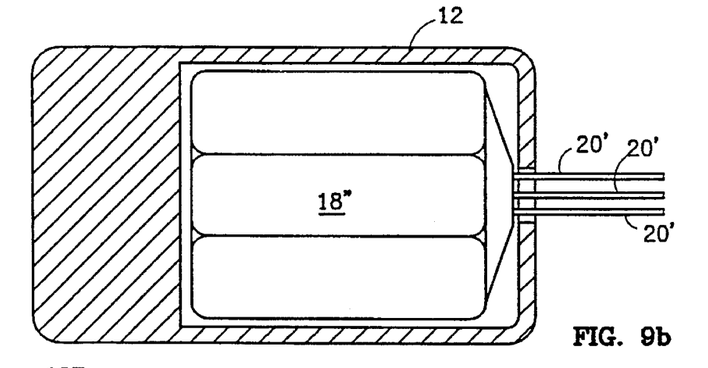
FIG. 9B is a top view of parallel fluid chambers in the fluid container. Specifically shown are three independent fluid chambers. These independent fluid chambers can be independently controlled to pass fluid by means of a manual clamp or occluder valve.

Another variation contemplated for fluid treatment bags of the invention is the use of multichambered bags. The multiple chambers can be associated in stacked or parallel orientation (see FIGS. 9A and 9B for examples of each orientation). Each of the individual chambers can be provided with their own independent ouput means, or a common output can be employed for the fluids contained in the individaul chambers. The delivery of fluid to a patient from the individual (or combined) contents of each chamber can be controlled in any suitable manner, e.g., by manual means, automatic means, or a combination thereof.

Figure 10A:
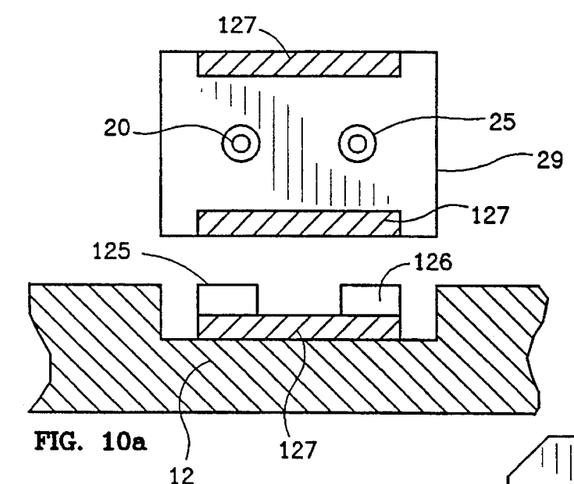
FIG. 10A illustrates an example construction employing a magnetically operated activator means wherein a Hall switch becomes actuated when the fluid treatment bag containing a soft iron bar therein is positioned within the containment means so as to complete the magnetic circuit.
Figure 10B:
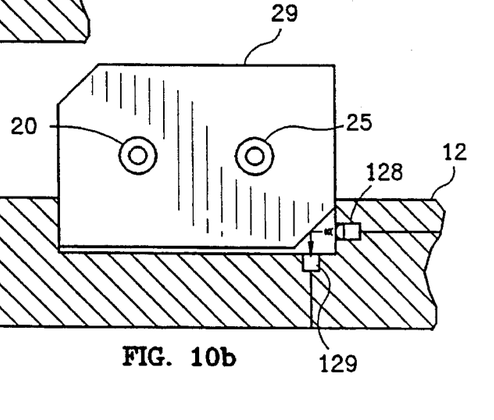
FIG. 10B illustrates an example of an optical activator means wherein light emitted from an LED is reflected onto a receiving detector by a surface associated with the fluid treatment bag, when the fluid treatment bag is properly positioned within the containment means of the invention pump. Thus, the presence of the reflective surface is indicative of the presence of the proper fluid treatment bag in the containment means.

Examples of activator means useful in the practice of the present invention include mechanical means (e.g., lock and key operation, switch, bag configuration (so that only the appropriate bag size and configuration will fit in the containment means), and the like), magnetic means (e.g., positioning a magnet in the containment means and a piece of ferrite in the fluid treatment bag, so that positioning of the treatment fluid bag in the containment means enables the control circuit; see, for example, FIG. 10A), electrical contact (so that appropriate positioning of the fluid treatment bag in the containment means completes a circuit required to enable the control circuit), optical coupling (so that the presence of the treatment fluid bag is required for the optical circuit to be completed; see, for example, FIG. 10B), and the like.

In addition to the activator means, the extension set of the invention treatment fluid bag optionally further comprises a built-in flow restrictor; fitment for attaching the treatment fluid bag to a needle or to a patient's catheter site; clamp to stop the flow of the treatment fluid before, during or after delivery of the treatment fluid to the patient; a filter in the tubing line; a check valve; and the like.

Inflatable bladder(s) contemplated for use in the practice of the present invention are constructed so as to be readily expandable, i.e., having a shape which incurs substantially no strain energy as the bladder is expanded to a size which corresponds to substantially the entire volume of the containment means in which the treatment fluid bag and bladder are positioned. Exemplary materials from which bladders useful in the practice of the invention can be prepared include polymeric materials, rubber-filled or polymer-filled cloth, and the like. Accordion-type bladders, pre-folded or pre-creased bladders, or any of a variety of other collapsible configurations are suitable.

It is also desirable to be able to controllably vent the bladder, so as to reduce the flow rate of treatment fluid from the bladder, terminate flow of treatment fluid, allow disassembly and servicing of the invention pump, and the like. Such venting can be accomplished in a variety of ways. For example, a vent having a pinch clamp thereon can be provided on the bladder. Alternatively, the drive fluid pump can be a reversible pump, so that the pump can be employed to remove drive fluid from the bladder. As another alternative, the latch means used to secure the base to the cover of the invention pump assembly can serve multiple purposes, i.e., latching the pump assembly, activating the unit electronically, and closing off the vent means for the bladder. Optionally, there may also be provided (as part of the pump assembly) means to assist in deflating/flattening the bladder once inflation thereof has been discontinued and a vent opened. This can be accomplished in a variety of ways, such as, for example, by incorporating a light-duty spring within the bladder (to aid in drawing the bladder down to its non-inflated size), by including a light-duty spring in the containment means (to aid in returning the bladder to its non-inflated size), by providing means to evacuate the bladder, and the like.

The means for impinging the bladder against the treatment fluid bag as the bladder is inflated can be provided in a variety of ways. For example, such means can be provided by containment members, which may comprise a variety of structures. Optionally, one or more of the containment members will include a member complementary to the activator means of the treatment fluid bag, so that the juxtaposition of containment member(s) and treatment fluid bag will cooperate to enable the means for controllably inflating the bladder to operate (when the means for controllably inflating said bladder is disabled in the absence of said activator means).

In one embodiment, a first containment member is a rigid platen having a planar surface and a second containment member is a rigid base having a receptacle formed therein to retain the drive fluid bladder and to receive the treatment fluid bag. The base and platen are removably engageable to fully enclose the bag and bladder. Guide members are preferably provided on the platen and base to enable slidable engagement thereof after placement of fluid treatment bag in the base. Preferably, a latch is further provided to securely lock engagement of the platen and base in place.

In another embodiment, a first containment member is a rigid platen having a receptacle formed therein to retain the drive fluid bladder and to receive the treatment fluid bag, and a second containment member is a rigid base having a planar surface. As with the previously described embodiment, the base and platen are removably engageable to fully enclose the bag and bladder. Guide members are preferably provided on the platen and base to enable slidable engagement thereof after placement of a fluid treatment bag in the platen. Preferably, a latch is further provided to securely lock engagement of the platen and base in place.

In yet another embodiment, a first containment member is a rigid platen having a planar surface. A second containment member is a flexible, yet substantially inelastic sheet, loosely attached to the platen at opposite sides to form a sling. The bladder is positioned in the sling and the infusion pump is assembled by sliding a treatment fluid bag into the sling in abutment with the bladder, and optionally attaching the outlet tube to the bag. In a preferred embodiment, the treatment fluid bag employed will include its own pre-attached extension set, optionally containing its own flow restrictor.

Containment members contemplated for use in the practice of the present invention can be formed from high-strength materials such as rigid plastics, flexible plastics, semi-rigid plastics, die-cast aluminum, and the like.

Means for controllably inflating the drive fluid bladder contemplated for use in the practice of the present invention are provided by a control assembly, which comprises a pressure sensor, in operative communication with a suitable control circuit, which is, in turn, in operative communication with a drive fluid pump. Optionally, the control assembly may contain a display for operator interface. Optionally, control assembly may also include a coordinating activator means, i.e., a member complementary to the activator means of the treatment fluid bag, so that the juxtaposition of the control assembly and treatment fluid bag will cooperate to enable the control assembly to operate (when the control assembly is disabled in the absence of such activator means associated with the fluid treatment bag).

The control assembly can be provided as an integral part of the pump of the invention, or can be provided as a separate module, so long as communication means is provided to introduce drive fluid from the drive fluid pump into the drive fluid bladder. Housing can be provided for the control assembly to be positioned internal to such housing, as shown, for example, in FIG. 1. Such control assembly housing can further be integral with the base and/or cover of the pump assembly. The pump assembly can further comprise an input station comprising a plurality of touch keys for entering operational commands to the control assembly. Alternatively, separate housing can be provided for the control assembly which is then employed as a separate module positioned in convenient proximity to the containment means in which the treatment fluid bag and drive fluid bladder are positioned.

Control circuits contemplated for use in the practice of the present invention provide means to establish a set point pressure, means for comparing the set point pressure to the actual pressure in the bladder (e.g., a comparator), and means capable of driving the drive fluid pump motor (e.g., a switch to turn on the motor). Such a control circuit can optionally contain an op-amp to amplify the pressure signal from the pressure sensor. Alternatively, a pressure switch can be employed to control the operation of the drive fluid pump.

In addition, control circuits contemplated for use in the practice of the present invention optionally further include means for monitoring the amount of fluid dispensed over time. This can be accomplished in a variety of ways, such as, for example, by monitoring the amount of time the pump is on during the period of delivery, by monitoring the number of revolutions the pump has made during the period of delivery, by monitoring the duty cycle of the pump during the period of delivery, and the like. Each of the above-described measures are proportional to the volume displaced by the pump, and thus can be used to readily determine the actual volume of fluid displaced during the time period of interest.

The additional information provided by monitoring the total volume of fluid delivered by the pump, in addition to controlling the rate of fluid delivery, allows one to check the operation of the pump over an extended period of time. Thus, after the pump has been in operation for a period of time, the actual volume of fluid delivered can be compared to the volume which the pump has theoretically delivered (based on the set delivery rate for the pump). If the desired volume of fluid has not been delivered, the flow rate can be adjusted accordingly. Alternatively, if a target total volume of fluid is sought to be delivered in a defined period of time, the ability to monitor the actual volume delivered over time would be useful to ensure that the desired volume of treatment fluid is actually delivered within the desired timeframe.

Drive fluid pumps contemplated for use in the practice of the present invention are readily available and are well known in the art of automatic blood pressure monitors. Any drive means capable of producing a positive displacement of drive fluid on each stroke can be employed. Examples include an eccentric cam driving a diaphragm, a bellows, and the like; various solenoid configurations driving a diaphragm, a bellows, and the like; a stepper motor with an axial lead screw shaft driving a diaphragm, a bellows, and the like; a rotary vein-type pump driven by a DC motor, a stepper motor, and the like; and so on.

Conventional flexible plastic medical tubing having a predetermined fixed inner diameter is suitable for use as the outlet tube employed in the practice of the present invention. A flow restrictor may optionally be positioned along the length of such tubing, intervening in the treatment fluid flowpath of the outlet tube. The presence of a flow restrictor serves to further narrow the inner diameter of the outlet tube to a reduced fixed inner diameter.

The treatment fluid flow rate through the outlet tube can be controlled in a variety of ways. According to one such control method, the treatment fluid flow rate is adjusted either up or down by correspondingly increasing or decreasing the drive fluid pump output and consequently the pressure in the bladder. For this purpose a pressure sensor is provided in fluid communication with the drive fluid bladder. The pressure sensor supplies pressure measurements to a control circuit regulating the pump output. Both the pressure sensor and control circuit are preferably retained within a control housing integral with one or both containment members. A command input station may also be provided on the housing in communication with the control circuit to enable an operator to program a specific sequence of operating parameters into the control circuit.

According to an alternate control method, the treatment fluid flow rate can be adjusted by increasing or decreasing the opening of the outlet tube by means of an occluder or restrictor positioned therealong. For example, the fluid flow rate can be adjusted to one of two levels, i.e., either full flow or no flow, by correspondingly opening or closing the outlet tube by means of an occluder. The occluder is preferably a clamp external to the outlet tube which operates by pinching off the flexible outlet tube to close it and releasing the tube to open it. For this purpose a control circuit is provided to dictate the position of the occluder. An input station in communication with the control circuit may also be provided to enable the operator to program a specific sequence of occluder operation as a function of time.

As those of skill in the art recognize, combination(s) of the above-described pressure control/flow control methodology can also be employed. For example, a flow profile defined by the drive fluid pump output can be further modified by the operation of an occluder or restrictor in combination therewith.

Optionally, the invention infusion pump further comprises a bubble detector, so as to ensure that substantially air-free fluid is delivered to the patient. Numerous means exist to detect the presence of bubbles in fluid-bearing tubing (e.g., infrared detection, ultrasonic detection, and the like), and those of skill in the art can readily select a suitable means for use with the invention infusion pump.

By employing a combination of control means in the practice of the present invention, external inputs from a variety of sources (e.g., manual input by the patient or a care-giver, electronic input derived from a suitable sensor (e.g., to monitor heartrate, blood pressure, blood chemistry, etc.), and the like) can be employed to adjust the flow rate at which treatment fluid is delivered to the patient.

Figures 1, 2:
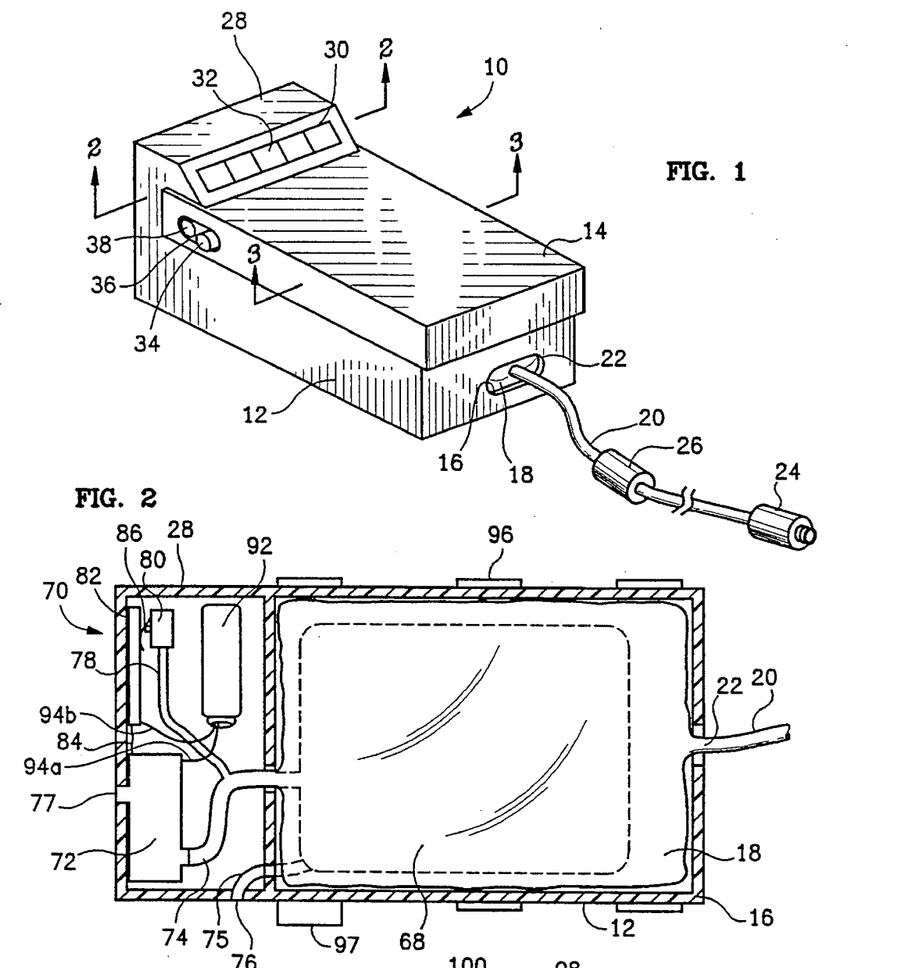
FIG. 1 is a perspective view of one embodiment of the infusion pump of the present invention.
FIG. 2 is a cross-sectional view as seen along line 2—2 in FIG. 1, wherein the cover plate of the infusion pump has been removed.

Referring now to FIG. 1, a first embodiment of an infusion pump of the present invention is shown and generally designated 10. Infusion pump 10 is housed within a pair of containment members, the lower containment member 12 being the base and the upper containment member 14 being a cover plate termed a platen. Retained within receptacle 16 formed by base 12 is a prefilled collapsible treatment fluid bag 18. Extending from bag 18 is a flexible outlet tube 20 which exits receptacle 16 via opening 22 in base 12. Tube 20 extends to a patient in whom the treatment fluid is to be intravenously infused. A site adaptor fitting 24 is provided at the end of tube 20 which enables communication between tube 20 and a vein of the patient.

Tube 20 is a conventional flexible plastic medical tubing having a predetermined fixed inner diameter. A flow restrictor 26 may optionally be positioned along tube 20 which intervenes in the treatment fluid flowpath of tube 20 to further narrow the inner diameter of tube 20 as originally manufactured to a reduced fixed inner diameter.

As shown in FIG. 1, housing 28 can be provided for a control assembly which, in this embodiment, is positioned internal to housing 28, as described hereafter. Control assembly housing 28, in this embodiment, is integral with base 12 and has an input station 30 on its face comprising a plurality of touch keys 32 for entering operational commands to the control assembly.

Positioned on cover plate 14 is a latch 34 extending from a latch opening 36 in plate 14. Latch 34 is provided for locking cover plate 14 in place upon engagement with base 12. Drive fluid vent 38 (formed in base 12) is preferably positioned in alignment with latch opening 36 and latch 34 when cover plate 14 engages base 12. Vent 38 enables discharge of drive fluid from a drive fluid bladder, which is retained within receptacle 16 described hereafter with reference to FIG. 2, when latch 34 is in the unlocked position as shown. Once latch 34 is slid into the locked position over vent 38, discharge of drive fluid is blocked.

In accordance with this embodiment, infusion pump 10 is further described with reference to FIG. 2 which shows the pump components internal to control assembly housing 28 and base 12 having cover plate 14 removed therefrom. Collapsible fluid treatment bag 18 is positioned to easily fit within receptacle 16 with outlet tube 20 extending therefrom via opening 22. Positioned beneath bag 18 and juxtaposed therewith is inflatable bladder 68 (shown in a deflated state). Operation of bladder 68 is under the control of a control assembly generally designated 70 which is contained within housing 28.

Assembly 70 comprises a drive fluid pump 72 in fluid communication with bladder 68 via drive fluid inlet tube 74. Bladder 68 has a drive fluid outlet tube 75 in fluid communication with a drive fluid outlet port 76. Pump 72 receives drive fluid from an external source, such as the ambient atmosphere, via drive fluid feed port 77. A pressure sensor tube 78 is in fluid communication with drive fluid inlet tube 74 to provide fluid communication between pressure sensor 80 and bladder 68. Pressure sensor 80 may be a pressure transducer having a linear output or a pressure switch having an on/off nonlinear output. Sensors suitable for this purpose include solid state sensors, mechanical sensors, capacitive sensors, reluctance-type sensors, and the like. Operational commands for assembly 70 are generated in a control circuit, e.g., a microprocessor, integral with electronics board 82. The control circuit may be preprogrammed or alternatively reprogrammable by means of input station 30 shown in FIG. 1.

Electronics board 82 electrically communicates with pump 72 and sensor 80 via lines 84 and 86, respectively. The components of assembly 70 can all be powered from a single electrical power source 92 which distributes power via lines 94a, 94b. Power source 92 may be an internal battery as shown here which is either replaceable, rechargeable, or simply disposable along with the entire infusion pump 10 upon use. Alternatively, the power source can be external to assembly 70 such as common household current.

Figure 3:
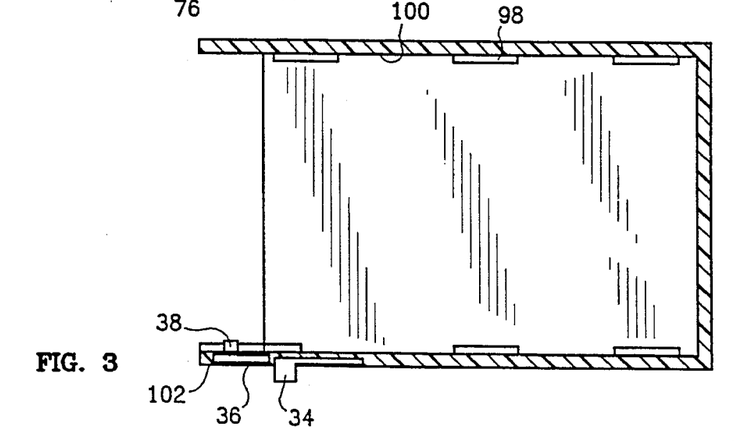
FIG. 3 is a cross-sectional view of the cover plate for the invention infusion pump, as seen along line 3—3 in FIG. 1.
Figure 4:
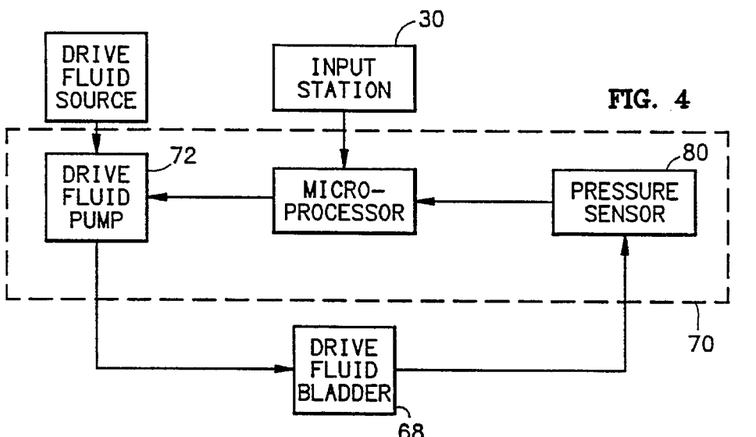
FIG. 4 is a schematic of the control assembly for the infusion pump shown in FIG. 2.

Base 12 and cover plate 14 can be fixably engaged in a variety of ways, such as, for example, by a combination of pivot means and latching means (wherein pivot means and latching means can be positioned on the front, side, or back of the base and/or cover plate, wherein the pivot means and latching means are preferably positioned on opposing sides of the base and/or cover plate), by slidable engagement of base and cover plate in combination with pivot means, by use of a latch which is actuated by the bladder as the bladder is inflated, and the like. As shown in FIG. 3 (which shows cover plate 14), a presently preferred means of such attachment comprises providing rail segments 96 and latch coupling 97 on the outside edge of base 12. The rail segments and latch coupling enable fixable engagement of base 12 and cover plate 14. Rail segments 98 are provided along the bottom of inside edge 100 of cover plate 14. Rail segments 98 are positioned to align beneath rail segments 96 of base 12 when cover 14 is slid over receptacle 16 of base 12. Latch 34 is positioned within latch opening 36 to lock rail segments 96, 98 in place relative to each other when latch 34 is hooked through slot 102 and over latch coupling 97 on base 12. When latch 34 is in the locked position, it plugs drive fluid vent 38 of cover 14 which is in alignment with port 76 of base 12 in fluid communication with bladder 68.

Figure 5:
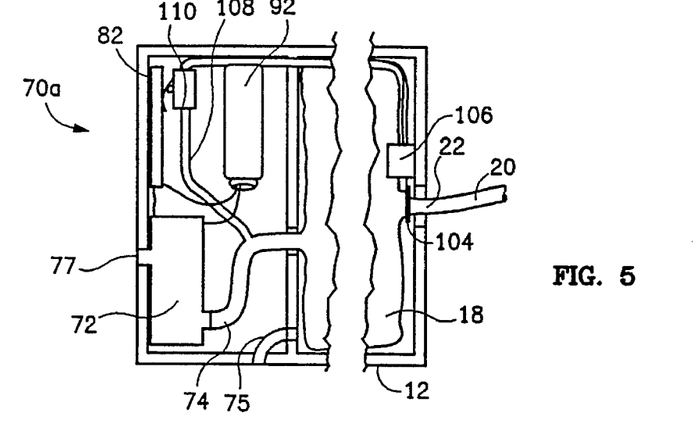
FIG. 5 is a broken cross-sectional view corresponding to the view of FIG. 3 showing another embodiment of the infusion pump of the present invention.

FIG. 5 shows an alternate embodiment of a control assembly generally designated 70a wherein occluder 104 is provided on tube 20 immediately inside opening 22 to enable closure of tube 20 and stoppage of treatment fluid flow therethrough as desired. An occluder motor 106 (e.g., a solenoid, a latching solenoid, a step-motor actuator, various mechanisms in cooperation with a motor, such as an over-the-center mechanism, eccentric cam actuator, and the like) adjacent occluder 104 and in communication with power source 92 and suitable control circuit, e.g., microprocessor, via lines 108 and 110, respectively, activates occluder 104 on command from the control circuit. A clock is further provided integral with electronics board 82 to provide control input to the control circuit. It is to be understood that although control assemblies 70 and 70a have been described above with reference to infusion pump 10, similar control assemblies can be provided with infusion pump 40 to perform the same function.

Figure 7:
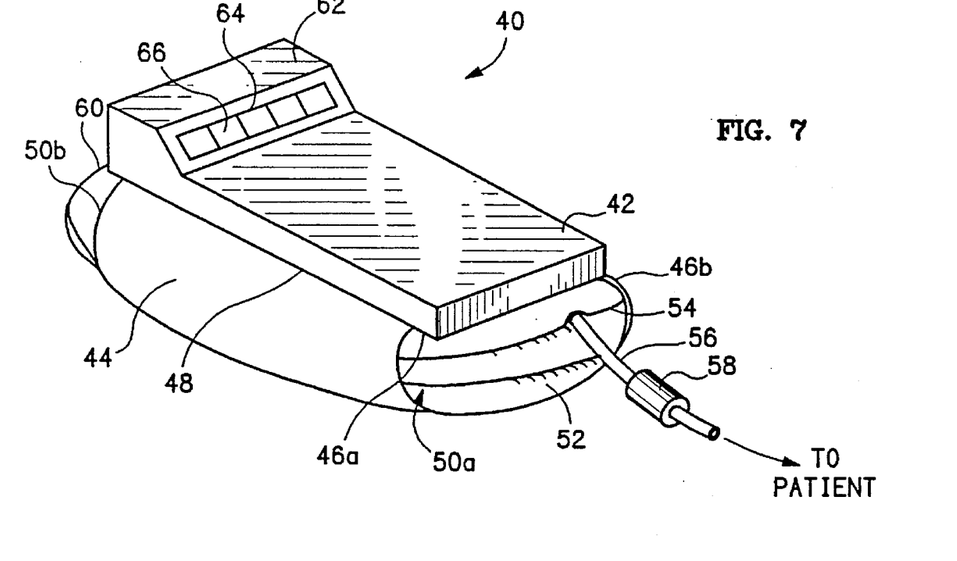
FIG. 7 is a perspective view of another embodiment of the infusion pump of the present invention.

FIG. 7 shows an alternate embodiment of the infusion pump of the present invention generally designated 40. Infusion pump 40, like infusion pump 10, has a pair of containment members including a rigid platen 42 as the upper containment member. The lower containment member 44, however, is a flexible, yet substantially inelastic and unstretchable sling preferably formed from a high-strength mesh or cloth fabric, such as a nylon mesh. Sling 44 has a rectangular shape having two opposing sides 46a, 46b fastened to the bottom 48 of platen 42 such that sling 44 hangs loosely therefrom with openings 50a, 50b at the front and back of sling 44, respectively.

An inflatable drive fluid bladder 52 is retained in sling 44. A collapsible treatment fluid bag 54 is removeably positioned in sling 44 juxtaposed with bladder 52. Positioning of bag 54 in sling 44 is accomplished by sliding prefilled bag 54 into sling 44 through either opening 50a or 50b, while bladder 52 is retained therein. Extending from bag 54 to the patient is treatment fluid outlet tube 56 having a site adaptor fitting (not shown) positioned at the end of tube 56 opposite bag 54 which enables intravenous infusion of the treatment fluid into the patient.

Tube 56 is a conventional flexible plastic medical tubing having a predetermined fixed inner diameter. A flow restrictor 58 may optionally be positioned along tube 56. Platen 42 is formed from a high-strength rigid material such as a rigid plastic. Collapsible bag 54 is a flexible plastic bag of the type conventionally used to retain medical treatment fluids for intravenous infusion. Bag 54 typically has a volumetric capacity larger than that of bag 18 of the first embodiment and is preferably between about 1000 ml and 5000 ml.

Inflatable drive fluid bladder 52 has a drive fluid tube 60 extending therefrom, through opening 50b, and into control assembly housing 62 where tube 60 connects to a drive fluid pump, thereby providing fluid communication between bladder 52 and the drive fluid pump described with reference to FIG. 2. Control assembly housing 62 is integral with platen 42 and has an input station 64 on its face comprising a plurality of touch keys 66 for entering operational commands to the control assembly contained within housing 62.

As used herein, the term "portable" pumps refers to pumps which are small enough (and lightweight enough) to carry around without the need for special transport means, operate on their own power source (without the need for an independent source of power), are rugged enough to withstand the impact of constant and/or frequent movement, and the like.

Figure 8:
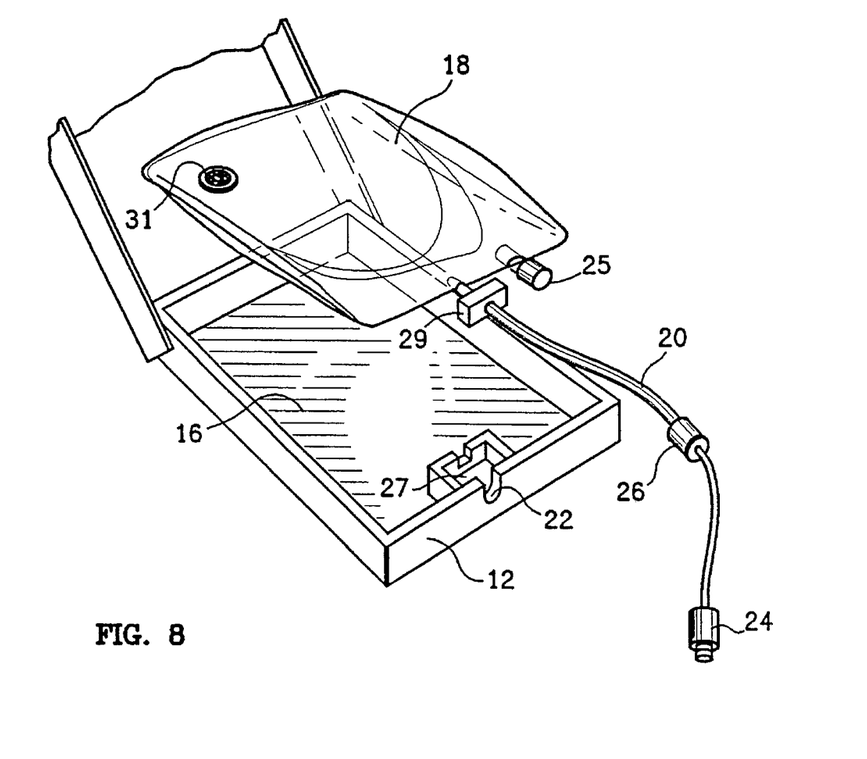
FIG. 8 is a schematic of a treatment fluid bag of the present invention.

An exemplary treatment fluid bag of the invention is shown in FIG. 8 wherein 12 refers to the base in which the treatment fluid bag is retained, 16 refers to the receptacle formed by base 12, 18 refers to the treatment fluid bag, 20 refers to flexible outlet tube, 22 refers to the opening in base 12 wherethrough the flexible outlet tube passes, 26 refers to the optional flow restrictor, 24 refers to a site adaptor fitting, 25 refers to the fill port; 31 refers to an air vent; and 27 and 29 refer to means to incorporate activator means into the containment means and treatment fluid bag of the invention, respectively.

OPERATION

Operation of pump 10 is now described with reference to FIGS. 1–5, it being further understood that the present operational description applies similarly to pump 40, as well as to other variations. Infusion of treatment fluid is performed in one instance by placing a prefilled treatment fluid bag 18 in receptacle 16 atop bladder 68 after cover 14 is removed from base 12. Outlet tube 20 is fed through opening 22.

Cover 14 is slid back onto base 12 such that rail segments 96 engage rail segments 98. The tight fit of bag 18 in receptacle 16 impinges bag 18 against bladder 68 as cover 14 is being positioned driving any residual drive fluid retained in bladder 68 out into the surrounding atmosphere via tube 74, port 76, and vent 38. The preferred drive fluid is ambient air. Latch 34 is then slid shut to lock cover 14 in place and seal off vent 38 from the atmosphere. Closing of latch 34 can cooperate with a switch (not shown) to activate drive fluid pump 72. In an alternate embodiment drive fluid pump 72 can be activated by the operator through a command to input station 30 which communicates with the control circuit of electronics board 82.

When drive fluid pump 72 is activated, it draws air through drive fluid feed port 77 and feeds it under pressure to bladder 68 via tube 74. The pressurized air inflates bladder 68 within the confined receptacle 16 impinging both bladder 68 and bag 18 against the inner surfaces of base 12 and cover 14. Once the treatment fluid bag is pressurized, the contents thereof can be purged of air (e.g., by opening the clamp and letting air out of the bag, then closing the clamp) and placed in communication with a desired vein of a patient using site adaptor 24 at the end of tube 22.

Bag 18 collapses at a rate proportional to the rate at which treatment fluid is expelled from the bag, thereby giving bladder 68 increasing amounts of space in which to expand. Bladder 68 can be inflated until it fills the entire volume of confined receptacle 16, thereby completely collapsing bag 18 and expelling treatment fluid therefrom, thereby delivering treatment fluid to the patient.

In the embodiment of FIG. 2, the flow rate of treatment fluid to the patient is governed by the fixed cross-sectional area of outlet tube 20 and the pumping pressure of drive fluid pump 72. A cross-sectional area of the tube can be selected other than its area of manufacture by fixing flow restrictor 58 on tube 20 to reduce its cross-sectional area. Variable flow rate adjustment is achieved by means of control assembly 70 shown in FIG. 2 and further shown schematically in FIG. 4 which acts as a feedback circuit. Whenever pressure sensor 80 measures too low a pressure, it is detected by the control circuit which sends a signal to drive fluid pump 72 to increase its output up to the desired level. If the measured pressure is too high, the control circuit conversely sends a signal to drive fluid pump 72 to decrease its output accordingly.

Figure 6:
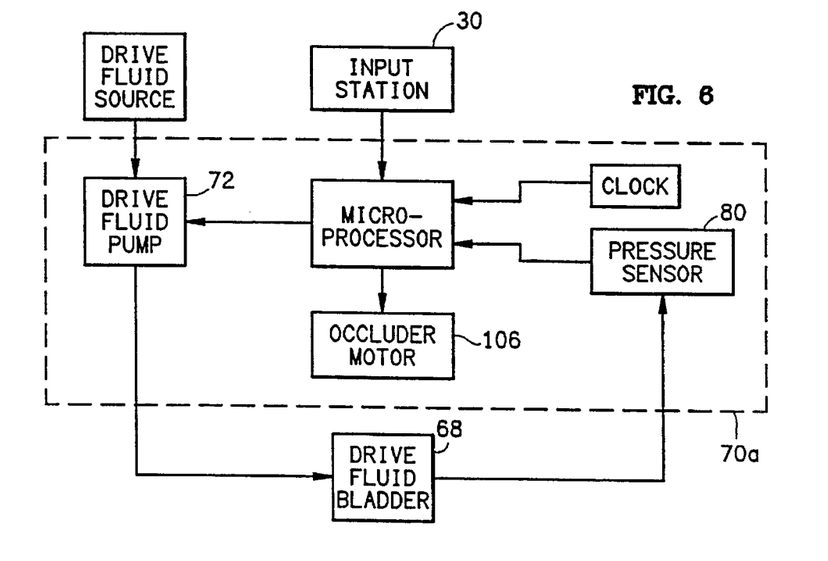
FIG. 6 is a schematic of the control assembly for the infusion pump shown in FIG. 5.

In the embodiment of FIG. 5 (also shown schematically in FIG. 6), treatment fluid flow rate is regulated by fully opening or closing tube 20 in correspondence with occluder 104. Operation of occluder 104 is governed by commands from the control circuit integral with electronics board 82 which further utilizes the clock also integral with electronics board 82 to determine tube 20 opening and closing times. In either control assembly embodiment, the operator can program additional control commands into the control circuit via input station 30 if desired.

The materials for construction of pumps 10 and 40 are generally and preferably selected to be both inexpensive and lightweight. This enables the pump of the present invention to be portable and, if desired, disposable after each of one or several uses.

While the particular infusion pumps as herein shown and disclosed in detail are fully capable of obtaining the objects and providing the advantages herein before stated, the disclosure is to be understood as merely illustrative of the presently preferred embodiments of the invention.

We claim:

1. A pump for infusing intravascular treatment fluid to a patient, said infusion pump comprising:

(1) a containment receptacle for receiving a removable, collapsible treatment fluid bag having an outlet tube for establishing fluid communication between the treatment fluid bag and the patient;

(2) an inflatable bladder positioned in the containment receptacle to exert force on the treatment fluid bag as the bladder is inflated when the treatment fluid bag is positioned within the containment receptacle;

(3) an electronic control system for electronically controlling pressure within the bladder so as to collapse the treatment fluid bag and controllably expel treatment fluid from the treatment fluid bag through the outlet tube.

2. A pump according to claim 1, wherein the treatment fluid bag includes an activator, and the electronic control system further includes an interaction device for interacting with the activator when present on a treatment fluid bag positioned within the receptacle to enable the electronic control system, the electronic control system being disabled in the absence of the activator.

3. A pump according to claim 2, wherein the activator and interaction device are mechanically operated.

4. A pump according to claim 2, wherein the activator comprises a selected configuration of the fluid bag, and the interaction device comprises a selected configuration of the containment receptacle, and wherein the electronic control system is enabled only when the fluid bag configuration is compatible with the receptacle configuration.

5. A pump according to claim 2, wherein the interaction device includes an electronic switch, wherein the activator positions the switch in a first position when the fluid bag is inserted within the receptacle and the activator positions the switch in a second position when the fluid bag is removed from within the receptacle.

6. A pump according to claim 2, wherein the activator and interaction device are magnetically operated.

7. A pump according to claim 6, wherein the activator comprises a magnetic substance and the interaction device comprises a magnet and a magnetically activated switch.

8. A pump according to claim 6, wherein the activator comprises a magnet and a magnetically activated switch and the interaction device comprises a magnetic substance.

9. A pump according to claims 7 or 8, wherein the magnetic substance is ferrite.

10. A pump according to claim 2, wherein the activator comprises a ferrite bar, and wherein the interaction device comprises a magnet and a magnetic switch which is actuated by the proximity of the ferrite bar.

11. A pump according to claim 2, wherein the activator and interaction device are electrically operated.

12. A pump according to claim 11, wherein the activator comprises a conductive element and the interaction device comprises an open electrical circuit, operatively coupled to the electronic control system, wherein the electrical circuit is completed by the conductive element when the fluid bag is properly inserted within the receptacle.

13. A pump according to claim 2, wherein the activator and interaction device are optically operated.

14. A pump according to claim 13, wherein the activator comprises a reflective surface of the fluid bag and the interaction device comprises a light source and a receiving detector.

15. A pump according to claim 14, wherein light emitted from the light source is reflected onto the reflective surface of the fluid bag onto the receiving detector when the fluid bag is properly positioned within the receptacle.

16. A pump according to claim 13, wherein the activator comprises a light source and the interaction device comprises a receiving detector.

17. A pump according to claim 1, further comprising an occluder for selectively, blocking treatment fluid flow across the outlet tube.

18. A pump according to claim 17, further comprising a control circuit in communication with the occluder for directing opening and closing the occluder as a function of time.

19. A pump according to claim 18, wherein an operator selectively controls the opening and closing of the occluder.

20. A pump according to claim 18, wherein the opening and closing of the occluder is under programmed control.

21. A pump according to claim 1, wherein the electronic control system includes a pressure sensor, in operative communication with a suitable electronic control circuit, which is, in turn, in operative communication with a drive fluid pump operatively coupled to the bladder.

22. A pump according to claim 1, further including means for venting the bladder.

23. A portable pump for infusing intravascular treatment fluid to a patient, the infusion pump comprising:
  (1) a containment receptacle for receiving a collapsible treatment fluid bag having an outlet tube for establishing fluid communication between the treatment fluid bag and the patient;
  (2) an inflatable bladder positioned in the containment receptacle to exert force on the treatment fluid bag as the bladder is inflated when the treatment fluid bag is positioned within the containment receptacle;
  (3) a pressure sensor positioned within the containment receptacle to detect force exerted by the bladder on the treatment fluid bag;
  (4) an electronic control assembly comprising a drive fluid pump in fluid communication with the bladder for inflating the bladder to collapse the treatment fluid bag and expel treatment fluid from the treatment fluid bag through the outlet tube, wherein the drive fluid pump is in operative communication with an electronic control circuit, which is, in turn, in operative communication with the pressure sensor.

24. A pump according to claim 23, wherein the treatment fluid bag includes an activator, and the electronic control assembly further includes an interaction device for interacting with the activator when present on a treatment fluid bag positioned within the receptacle to enable the electronic control assembly, the electronic control assembly being disabled in the absence of the activator.

25. A pump according to claim 23, further including means for venting the bladder.

26. A pump according to claim 23, further comprising an occluder for selectively blocking treatment fluid flow across the outlet tube.

27. A pump according to claim 26, further comprising a control circuit in communication with the occluder for directing opening and closing the occluder as a function of time.

28. A pump according to claim 27, wherein an operator selectively controls the opening and closing of the occluder.

29. A pump according to claim 27, wherein the opening and closing of the occluder is under programmed control.

\* \* \* \* \*